(12) United States Patent
Borkholder et al.

(10) Patent No.: US 9,668,689 B2
(45) Date of Patent: Jun. 6, 2017

(54) EVENT DOSIMETER DEVICE AND METHODS THEREOF

(71) Applicants: David A. Borkholder, Canandaigua, NY (US); Gregory T. A. Kovacs, Palo Alto, CA (US); Jeffrey Rogers, Alexandria, VA (US)

(72) Inventors: David A. Borkholder, Canandaigua, NY (US); Gregory T. A. Kovacs, Palo Alto, CA (US); Jeffrey Rogers, Alexandria, VA (US)

(73) Assignees: Rochester Institute of Technology, Rochester, NY (US); Defense Advanced Research Projects Agency, Arlington, VA (US)

( * ) Notice: Subject to any disclaimer, the term of this patent is extended or adjusted under 35 U.S.C. 154(b) by 0 days.

(21) Appl. No.: 15/130,074

(22) Filed: Apr. 15, 2016

(65) Prior Publication Data
US 2016/0228045 A1 Aug. 11, 2016

Related U.S. Application Data

(62) Division of application No. 13/371,183, filed on Feb. 10, 2012, now Pat. No. 9,339,224.
(Continued)

(51) Int. Cl.
*A61B 5/103* (2006.01)
*A61B 5/00* (2006.01)
(Continued)

(52) U.S. Cl.
CPC .......... *A61B 5/4064* (2013.01); *A61B 5/1112* (2013.01); *A61B 5/165* (2013.01);
(Continued)

(58) Field of Classification Search
CPC ...... A61B 5/4528; A61B 5/1071; A61B 5/103
(Continued)

(56) References Cited

U.S. PATENT DOCUMENTS 4,264,310 A 4/1981 Ashworth et al.
5,117,695 A 6/1992 Henderson et al.
(Continued)

FOREIGN PATENT DOCUMENTS

EP 1099389 A1 5/2001
EP 1408336 A3 6/2005
(Continued)

OTHER PUBLICATIONS

PCT International Search Report; PCT/US2012/026627 mailed Dec. 20, 2012.
(Continued)

*Primary Examiner* — Daniel Cerioni
(74) *Attorney, Agent, or Firm* — Joseph M. Noto; Bond, Schoeneck & King PLLC

(57) ABSTRACT

A method including a dosimetry device having at least one sensor in a housing and a dosimetry processing device with a memory. The dosimtery processing device is coupled to the at least one sensor in the housing. The dosimetry processing device is configured to execute programmed instructions stored in the memory comprising: obtaining readings from the sensor; storing the readings; conducting an analysis of the stored readings to determine an injury risk assessment; and outputting at least one of the conducted analysis of the determined injury risk assessment or the stored readings.

25 Claims, 2 Drawing Sheets

Related U.S. Application Data

(60) Provisional application No. 61/446,382, filed on Feb. 24, 2011.

(51) Int. Cl.

| | | |
|---|---|---|
| *F41H 1/02* | (2006.01) | |
| *F41H 1/04* | (2006.01) | |
| *F42D 5/00* | (2006.01) | |
| *A61B 5/11* | (2006.01) | |
| *A61B 5/16* | (2006.01) | |

(52) U.S. Cl.
CPC ............ *A61B 5/6803* (2013.01); *F41H 1/02* (2013.01); *F41H 1/04* (2013.01); *F42D 5/00* (2013.01); *A61B 2562/0219* (2013.01); *A61B 2562/0247* (2013.01); *Y10T 29/49002* (2015.01)

(58) Field of Classification Search
USPC ........................................................ 600/595
See application file for complete search history.

(56) References Cited

U.S. PATENT DOCUMENTS

| | | |
|---|---|---|
| 5,212,984 A | 5/1993 | Norling et al. |
| 5,220,838 A | 6/1993 | Fung et al. |
| 5,277,068 A | 1/1994 | Fukiura et al. |
| 5,357,808 A | 10/1994 | Fung et al. |
| 5,438,875 A | 8/1995 | Fung et al. |
| 5,524,489 A | 6/1996 | Twigg |
| 5,539,935 A | 7/1996 | Rush, III |
| 5,546,609 A | 8/1996 | Rush, III |
| 5,551,279 A | 9/1996 | Quick |
| 5,621,922 A | 4/1997 | Rush, III |
| 5,646,349 A | 7/1997 | Twigg et al. |
| 5,719,336 A | 2/1998 | Ando et al. |
| 5,723,787 A | 3/1998 | Stoddard et al. |
| 5,856,520 A | 1/1999 | Hirako et al. |
| 5,856,620 A | 1/1999 | Okada |
| 5,884,203 A | 3/1999 | Ross |
| 5,890,569 A | 4/1999 | Goepfert |
| 5,978,972 A | 11/1999 | Stewart et al. |
| 6,092,424 A | 7/2000 | Skinner et al. |
| 6,125,686 A | 10/2000 | Haan et al. |
| 6,178,820 B1 | 1/2001 | Kirjavainen et al. |
| 6,301,718 B1 | 10/2001 | Rigal |
| 6,307,481 B1 | 10/2001 | Lehrman et al. |
| 6,349,201 B1 | 2/2002 | Ford |
| 6,397,151 B1 | 5/2002 | Yamagish et al. |
| 6,501,386 B2 | 12/2002 | Lehrman et al. |
| 6,584,852 B2 | 7/2003 | Suzuki et al. |
| 6,661,347 B2 | 12/2003 | Lehrman et al. |
| 6,703,939 B2 | 3/2004 | Lehrman et al. |
| 6,711,951 B2 | 3/2004 | Kicher et al. |
| 6,730,047 B2 | 5/2004 | Socci et al. |
| 6,798,392 B2 | 9/2004 | Hartwell et al. |
| 6,826,509 B2 | 11/2004 | Crisco, III et al. |
| 6,864,796 B2 | 3/2005 | Lehrman et al. |
| 6,941,952 B1 | 9/2005 | Rush, III |
| 7,054,784 B2 | 5/2006 | Flentov et al. |
| 7,095,331 B2 | 8/2006 | Lehrman et al. |
| 7,145,461 B2 | 12/2006 | Lehrman et al. |
| 7,150,048 B2 | 12/2006 | Buckman |
| 7,150,191 B2 | 12/2006 | Foote et al. |
| 7,162,392 B2 | 1/2007 | Vock et al. |
| 7,194,903 B2 | 3/2007 | Dwyer |
| 7,194,905 B2 | 3/2007 | Yamamoto et al. |
| 7,318,349 B2 | 1/2008 | Vaganov et al. |
| 7,378,954 B2 | 5/2008 | Wendt |
| 7,384,380 B2 | 6/2008 | Reinbold et al. |
| 7,386,401 B2 | 6/2008 | Vock et al. |
| 7,404,324 B2 | 7/2008 | Braman et al. |
| 7,478,108 B2 | 1/2009 | Townsend et al. |
| 7,479,890 B2 | 1/2009 | Lehrman et al. |
| 7,526,389 B2 | 4/2009 | Greenwald et al. |
| 7,540,193 B2 | 6/2009 | Sato et al. |
| 7,609,156 B2 | 10/2009 | Mullen |
| 7,660,692 B2 | 2/2010 | Van Albert et al. |
| 7,693,668 B2 | 4/2010 | Vock et al. |
| 7,747,415 B1 | 6/2010 | Churchill et al. |
| 7,836,771 B2 | 11/2010 | Killion |
| 7,845,226 B2 | 12/2010 | Ohkoshi |
| 7,849,740 B2 | 12/2010 | Nichol |
| 7,992,421 B2 | 8/2011 | Jeftic-Stojanovski et al. |
| 8,056,391 B2 | 11/2011 | Petelenz et al. |
| 8,079,247 B2 | 12/2011 | Russell et al. |
| 8,145,441 B2 | 3/2012 | Xi |
| 2002/0183657 A1 | 12/2002 | Socci et al. |
| 2003/0197608 A1 | 10/2003 | Rudhard et al. |
| 2004/0171969 A1 | 9/2004 | Socci et al. |
| 2004/0200967 A1 | 10/2004 | Russell |
| 2005/0177335 A1 | 8/2005 | Crisco, III et al. |
| 2005/0177929 A1 | 8/2005 | Greenwald et al. |
| 2006/0038694 A1 | 2/2006 | Naunheim et al. |
| 2006/0074338 A1 | 4/2006 | Greenwald et al. |
| 2006/0189852 A1 | 8/2006 | Greenwald et al. |
| 2006/0282021 A1 | 12/2006 | DeVaul et al. |
| 2007/0056081 A1 | 3/2007 | Aspray |
| 2007/0079149 A1 | 4/2007 | Sahu et al. |
| 2007/0113702 A1 | 5/2007 | Braman et al. |
| 2007/0144396 A1 | 6/2007 | Hamel et al. |
| 2008/0006093 A1 | 1/2008 | Ueya |
| 2008/0072088 A1 | 3/2008 | Allarey et al. |
| 2008/0134794 A1 | 6/2008 | Jonsson |
| 2008/0151456 A1 | 6/2008 | Julicher |
| 2008/0256687 A1 | 10/2008 | Spencer |
| 2008/0281234 A1 | 11/2008 | Goris et al. |
| 2009/0000377 A1 | 1/2009 | Shipps et al. |
| 2009/0090190 A1 | 4/2009 | Ueya |
| 2009/0185700 A1 | 7/2009 | Suzuki |
| 2009/0267783 A1 | 10/2009 | Vock et al. |
| 2010/0005571 A1 | 1/2010 | Moss et al. |
| 2010/0016685 A1 | 1/2010 | Muehlsteff et al. |
| 2010/0072380 A1 | 3/2010 | Britton, Jr. et al. |
| 2010/0073678 A1 | 3/2010 | Smith et al. |
| 2010/0096556 A1 | 4/2010 | Arsalan et al. |
| 2010/0098269 A1 | 4/2010 | Abolfathi et al. |
| 2010/0102970 A1 | 4/2010 | Hertz |
| 2010/0121226 A1 | 5/2010 | Ten Kate et al. |
| 2010/0171514 A1 | 7/2010 | Bernstein |
| 2010/0179389 A1 | 7/2010 | Moroney, III et al. |
| 2010/0229784 A1 | 9/2010 | Bayne et al. |
| 2010/0257932 A1 | 10/2010 | Braman et al. |
| 2010/0275676 A1 | 11/2010 | King et al. |
| 2010/0307223 A1 | 12/2010 | Jeftic-Stojanovski et al. |
| 2010/0326192 A1 | 12/2010 | Petelenz et al. |
| 2011/0012759 A1 | 1/2011 | Yin |
| 2011/0077865 A1 | 3/2011 | Chen et al. |
| 2011/0098934 A1 | 4/2011 | Hubler et al. |
| 2011/0144539 A1 | 6/2011 | Ouchi |
| 2011/0144542 A1 | 6/2011 | Jin et al. |
| 2011/0152727 A1 | 6/2011 | Ten Kate |
| 2011/0162433 A1 | 7/2011 | Peng et al. |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184319 A1 | 7/2011 | Mack et al. |
| 2011/0184663 A1 | 7/2011 | Mack et al. |
| 2011/0199216 A1 | 8/2011 | Flinsenberg et al. |
| 2011/0201972 A1 | 8/2011 | Ten Kate |
| 2011/0203347 A1 | 8/2011 | Hower et al. |
| 2011/0230791 A1 | 9/2011 | Ten Kate et al. |
| 2011/0231145 A1 | 9/2011 | Chen |
| 2011/0246114 A1 | 10/2011 | Jin |
| 2011/0283791 A1 | 11/2011 | Jeftic-Stojanovski et al. |
| 2011/0290018 A1 | 12/2011 | Jeftic-Stojanovski et al. |
| 2012/0109575 A1 | 5/2012 | Balbus et al. |
| 2012/0223833 A1 | 9/2012 | Thomas et al. |

FOREIGN PATENT DOCUMENTS

| | | |
|---|---|---|
| EP | 2136215 A2 | 12/2009 |
| JP | 2004-117372 | 4/2004 |

(56) References Cited

FOREIGN PATENT DOCUMENTS

| WO | 2006-080880 |    | 8/2006 |
|----|-------------|----|--------|
| WO | 2007-083329 | A1 | 7/2007 |
| WO | 2008-051657 |    | 5/2008 |
| WO | 2009-026903 | A1 | 3/2009 |
| WO | 2009-070886 | A1 | 6/2009 |

OTHER PUBLICATIONS

PCT Written Opinion of the International Searching Authority; PCT/US2012/026627 mailed Dec. 20, 2012.
Riel et al., "Self-Indicating Radiation Alert Dosemeter (SIRAD)", Radiation Protection Dosimetry, 2006, pp. 1-4, doi: 10.1093/rpd/nci541, Oxford University Press.
Rochester Institute of Technology, "Faculty Connects Technology and Physiology to Improve Information about Effects of Explosive Blasts; Wearable Blast Dosimeter for Soldiers Measures Pressure and Head Acceleration," Athenaeum Article, 2 pages, Oct./Nov. Issue.

EVENT DOSIMETER DEVICE AND METHODS THEREOF

This application claims the benefit of U.S. application Ser. No. 13/371,183 filed Feb. 10, 2012, which claims the benefit of U.S. Provisional Patent Application Ser. No. 61/446,382 filed Feb. 24, 2011, which is hereby incorporated by reference in its entirety.

This invention was made with government support under contract no. HR0011-10-C-0095 awarded by the DARPA. The government has certain rights in the invention.

BACKGROUND

Traumatic brain injury (TBI) from an explosive blast remains a significant problem for military personnel, especially those involved in counter insurgency operations. Mild to moderate TBI may be difficult to detect immediately post event, with cognitive or motor deficits manifesting weeks or months post event.

Currently, there is no widely deployed system to dose the exposure to explosive blast. Given the nature of TBI, the wide variability in explosions and physical configurations during a blast, and variability in human response to each blast, a widely deployed system to all personnel in a theater is needed to build a database of sufficient size to allow real-time dosimeter data to be used for triage.

SUMMARY

A dosimetry device includes at least one sensor in a housing and a dosimetry processing device with a memory. The dosimtery processing device is coupled to the at least one sensor in the housing. The dosimetry processing device is configured to execute programmed instructions stored in the memory comprising: obtaining readings from the at least one sensor; storing the readings; conducting an analysis of the stored readings to determine an injury risk assessment and outputting at least one of the stored readings or the conducted analysis of the determined injury risk assessment.

A method for using at least one dosimetry device includes securing at least one dosimetry device to one or more different locations on an object. The dosimetry device includes a dosimetry processing device with a memory coupled to at least one sensor in a housing. The dosimetry processing device obtains readings from the at least one sensor and stores the readings. The dosimetry processing device conducts an analysis of the stored readings to determine an injury risk assessment and outputs at least one of the stored readings or the conducted analysis of the determined injury risk assessment.

A dosimetry device includes at least one sensor in a housing, a global positioning device coupled to the dosimetry processing device, and a dosimetry processing device with a memory. The dosimetry processing device is coupled to the at least one sensor and the global positioning device in the housing. The dosimetry processing device is configured to execute programmed instructions stored in the memory comprising: obtaining readings from the at least one sensor; storing the readings; storing location data from the global positioning device with the obtained readings; and outputting the stored readings and the location data.

A method for using at least one dosimetry device includes securing at least one dosimetry device to one or more different locations on an object. The dosimetry device includes a dosimetry processing device with a memory coupled to at least one sensor in a housing. The dosimetry device obtains readings from the sensor, stores location data from the global positioning device with the obtained readings, and outputs the stored readings and the location data.

This technology provides a number of advantages including providing a more effective and efficient event monitoring dosimetry apparatus. With this technology, event data from an explosion, blast, blow or other event can be captured and utilized to provide real time information on obtained readings and/or conducted analyses with or without location data. The analyses can include determination of an injury risk assessment that can be used for triage. Additionally, this technology can capture and provide event data that will help to provide a better understanding the mechanisms of traumatic and other brain injuries resulting from an explosion, blast, blow or other event This technology can be used in a variety of different applications, such as for the military, sporting activities, and other daily activities by way of example only. For military applications, this technology could be helmet mounted, helmet strap mounted, worn on the torso, mounted within vehicle cabins, on vehicle exteriors, and/or on buildings by way of example only. For sporting activities, this technology could be mounted within helmets, helmet straps, headbands, caps, and/or on uniforms by way of example only. For daily activities, this could be mounted to helmets used for bicycles and motorcycles by way of example.

DETAILED DESCRIPTION

Figure 1:
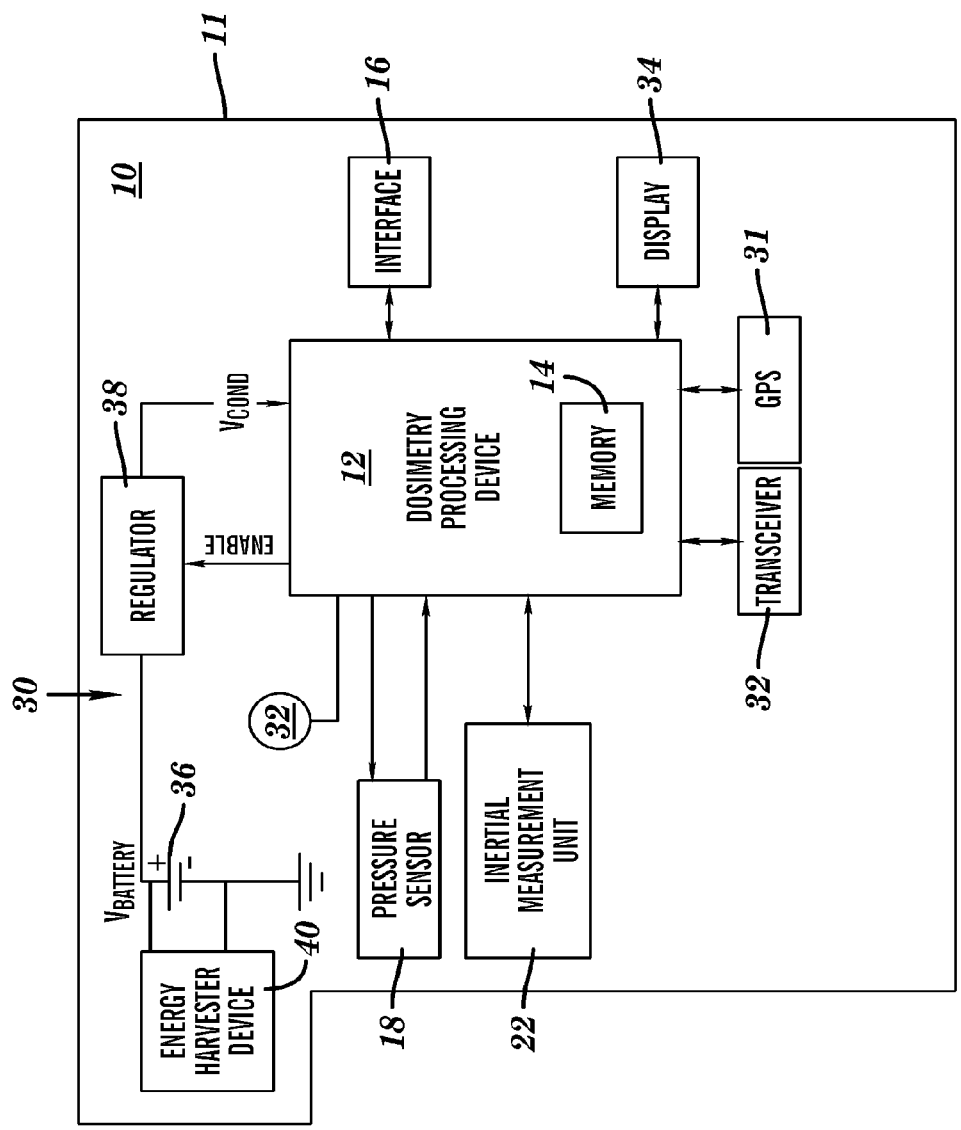
FIG. 1 is a diagram of an exemplary event monitoring dosimetry apparatus.

An exemplary event monitoring dosimetry apparatus 10 is illustrated in FIG. 1-. The event monitoring dosimetry apparatus 10 includes a housing assembly 11 with a dosimetry processing device 12 with a memory 14, an interface device 16, a pressure sensor 18, an inertial monitoring unit 22, a power system 30, a global positioning system 31, an engagement device 32, and display 34, although the apparatus 10 could include other types and numbers of systems, devices, components and elements in other configurations. This technology provides a number of advantages including provide a more effective and efficient event monitoring dosimetry apparatus.

Referring more specifically to FIG. 1, the dosimetry processing device 12 comprises one or more processors internally coupled to the memory 14, although other numbers and types of systems, devices, components, and elements in other configurations and locations can be used. The one or more processors in the dosimetry processing device 12 executes a program of stored instructions for one or more aspects of the present technology as described and illustrated by way of the examples herein, although other types and numbers of processing devices and logic could be used and the processor could execute other numbers and types of programmed instructions. A variety of different types of processors can be used.

Figure 2:
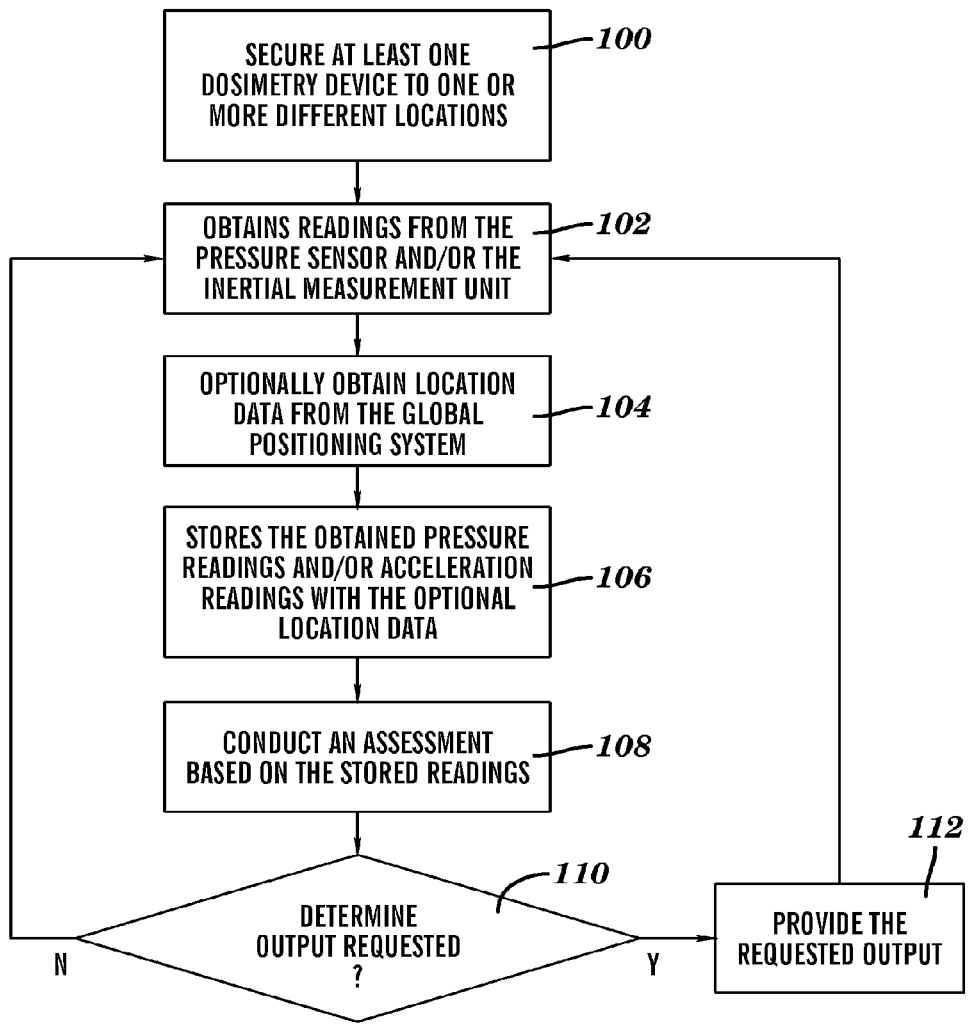
FIG. 2 is an exemplary method for monitoring events with the exemplary event monitoring dosimetry apparatus.

The memory 14 in the dosimetry processing device 12 stores these programmed instructions for one or more aspects of the present technology as described and illustrated herein, although some or all of the programmed instructions could be stored and executed elsewhere. A variety of different types of memory storage devices, that are coupled to the one or more processors in the dosimetry processing device 12, can be used for the memory 14 in the dosimetry processing device 12, such as a solid state memory by way of example. The flow chart shown in FIG. 2 is representative of example steps or actions of this technology that may be embodied or expressed as one or more non-transitory computer or machine readable instructions stored in memory 14 that may be executed by the one or more processors.

The interface device 16 in the dosimetry processing device 12 is used to operatively couple and communicate between the dosimetry processing device 12 and one or more external computing or storage devices, although other types and numbers of communication networks or systems with other types and numbers of connections and configurations can be used. In this example, the interface device 16 is a USB port, although other types and numbers of hard wired or wireless interfaces can be utilized.

Although an example of the dosimetry processing device 12 is described herein, it can be implemented on any suitable computer system or computing device. It is to be understood that the devices and systems of the examples described herein are for exemplary purposes, as many variations of the specific hardware and software used to implement the examples are possible, as will be appreciated by those skilled in the relevant art(s).

Furthermore, the system of the examples may be conveniently implemented using one or more general purpose computer systems, microprocessors, digital signal processors, and micro-controllers, programmed according to the teachings of the examples, as described and illustrated herein, and as will be appreciated by those ordinary skill in the art.

The examples may also be embodied as a non-transitory computer readable medium having instructions stored thereon for one or more aspects of the present technology as described and illustrated by way of the examples herein, as described herein, which when executed by a processor, cause the processor to carry out the steps necessary to implement the methods of the examples, as described and illustrated herein.

The pressure sensor 18 is coupled to the dosimetry processing device 12, although the pressures sensor 18 could be coupled to other types and numbers of devices. In this example, the pressure sensor 18 is a single pressure sensor, although other types and numbers of pressure sensors could be used.

Referring back to FIG. 1, the inertial monitoring unit 22 is a low-g (for example <16 g) three-axis accelerometer to capture linear acceleration in three axes, although other types such as a high-g (for example >100 g) and numbers of inertial measurement units could be used in other combinations. For example, the inertial measurement unit 22 could be a higher-g accelerometer or a gyroscope which records rotational acceleration.

The power system 30 includes a battery 36 coupled between a regulator 38 and an energy harvester device 40, although other types of power systems with other types and numbers of components, such as one without an energy harvester and/or without a regulator 38 could be used. In this example, the battery 36 is non-rechargeable and non-user replaceable so the dosimetry apparatus is designed to be disposable by way of example only, although other types of batteries can be used, such as a user-replaceable and rechargeable batteries. With this exemplary disposable design and the associated lower cost, multiple dosimetry apparatuses 10 may be utilized on each person which improves the quality of the collected data and the resulting injury risk assessments. Additionally, with this disposable design for this example of the dosimetry apparatus it is easier to incorporate design changes and update algorithms as the dosimetry apparatus is rolled out for product shipments. As a result, with this exemplary design the latest version always is being delivered out to customers in the field, while traditional (non-disposable) systems would have to somehow incorporate an upgrade. The regulator 38 is coupled to regulate power provided by the battery 36 to the dosimetry processing device 12. The energy harvester device 40, such as solar or vibration energy device by way of example only, can be used to supply power to the system and/or recharge the battery 36, although other types and numbers of energy harvester devices could be used.

An optional global position system (GPS) 31 is coupled to the dosimetry processing device 12 to provide location data for the dosimetry apparatus which can be correlated with and stored with the obtained sensor readings, although other types and numbers of location determination systems could be used.

The engagement device 32 is coupled to the dosimetry processing device 12, although the engagement device could be coupled in other manners and other types and numbers of engagement devices, such as a button, could be used. The engagement device 32 can be used to request an output of readings including of identified events and analyses of the readings to provide immediate triage. Additionally, other types and numbers of mechanisms for engaging the dosimetry processing device 12 can be used.

The display device 34 is used to provide a status indication for the output stored readings and/or of the analysis of the stored readings associated with identified events to provide immediate triage of the severity of an event, although other types and numbers of displays which provide other types of outputs can be used.

Referring to FIG. 2, an exemplary method for monitoring events with the exemplary event monitoring dosimetry apparatus will now be described. At step 100, at least one dosimetry apparatus 10 is secured to a location on an object, although other manners for securing the one or more dosimetry apparatuses 10 to the object can be used, such as detachable securing can be used.

In step 102, the dosimetry processing device in the dosimetry apparatus 10 obtains readings from the at least one of the pressure sensor 18 or the inertial measurement unit 22, although the dosimetry apparatus 10 can obtain readings from both as well as from other types and numbers of sensors. In this example, the pressure sensor 18 is a single pressure sensor which obtains pressure readings. Additionally, in this example, the inertial measurement unit 22 is a three-axis accelerometer which obtains linear acceleration readings in real time, although other types of inertial measurement units can be used, such as a gyroscope which obtains rotational acceleration readings.

In step 104, the dosimetry processing device 12 optionally may obtain location data from the global positioning system 31 which is correlated with the obtained sensor readings, although other types of positional information could be obtained.

In step 106, the dosimetry processing device 12 stores the obtained pressure readings from the pressure sensor 18 and/or acceleration readings from the inertial measurement unit 22 with the location data from the global positioning device 31 (if obtained) in memory 14, although other types and amounts of readings and other data could be stored in other locations and manners. For example, the dosimetry processing device 12 may select a smaller subset of the information, such as portions of the obtained pressure readings from the pressure sensor 18, the acceleration readings from the inertial measurement unit 22, and/or the location data from the global positioning device 31 for storage. Additionally, the global positioning device 31 also may be coupled to an emergency beacon or other transmitter or transceiver 32 in the dosimetry apparatus 10 that provides a coded or other data report to a designated device or other system about a blast or other exposure event, such as blast location and severity for an entity with the dosimetry apparatus 10.

In step 108, the dosimetry processing device 12 also may conduct a real time analysis of the obtained pressure and/or acceleration readings to determine an injury risk assessment based on the conducted analysis, although other types and numbers of analyses based on other types and numbers of sensors can be performed, such as conducing the injury risk assessment based on obtained readings from multiple sensors. In this example, the obtained readings may be compared by the dosimetry processing device 12 against stored tables of threshold readings in memory 14 to identify when one or more of the obtained readings are above the corresponding stored threshold reading in the table to identify an event. Additionally, the dosimetry processing device 12 conduct an analysis of the severity of the event based on an amount the one or more of the obtained readings are above the corresponding stored threshold reading in the table, although other manners for conducting an analysis can be used. The dosimetry processing device 12 stores the conducted analysis in memory 14, although the conducted analyses can be stored in other locations and manners and other types of processing of the conducted analyses and data could be executed. For example, the dosimetry processing device 12 may utilize captured readings and conducted analyses associated with particular individuals to tailor and adjust criteria and thresholds for each of these individuals, based on historical medical data, such as individual medical history data, individual injury historical data, or historical group medical data, such as readings and resulting assessments obtained by other dosimetry apparatuses 10 over a period of time, by way of example only. The criteria, thresholds and other metrics could be automatically adjusted by the dosimetry processing device 12 based on the data obtained above, although other manners for making these adjustments could be made, such as presenting a GUI to an operator to enter adjustments.

In step 110, the dosimetry processing device 12 determines whether an output is requested, such as by activation of the engagement device 32 or a request via the interface 16, such as a USB, from another computing device, although other manners for output requests could be used. The activating of the engagement device could trigger a display on display device 34, although other types of outputs could be triggered, such as an output of data and other information. The engagement device 32 also can have other functions, such as outputting different information based on a number of times the button is pressed or the length of time the button is pressed or powering on or off the dosimetry apparatus 10. The request for data through the interface 16 from another computing device can be for all or requested portions of the stored data. If in step 110, the dosimetry processing device 12 determines an output has not been requested, then the No branch is taken back to step 102 as described earlier. If in step 110, the dosimetry processing device 12 determines an output has been requested, then the Yes branch is taken to step 112.

In step 112, the dosimetry processing device 12 provides the requested output, such as a display on one of the display device 34 or via a request and response via the interface 16 and processed by dosimetry processing device 14, comprising at least a portion of one or more of the stored readings, the identified event, a determined injury risk assessment based on the conducted analysis, data relating to output requests, and/or any related data by way of example only, although the information could be output to other devices, other types and amounts of information and other data could be provided and the information and data can be obtained in other manners, such as through a connection with another computing device interacting with the dosimetry processing device 12 via the interface 16. Next, this method can return back to step 102 until the exemplary dosimetry apparatus 10 is turned off or the power runs out Accordingly, as illustrated and described with reference to the examples herein this technology provides a more effective and efficient event monitoring dosimetry apparatus. With this technology, event data from an explosion, blast, blow or other event can be captured and utilized to provide real time information on obtained readings and/or conducted analyses with or without location data. The technology can provide a real time assessment of risk injury to guide triage immediately post event. The detailed event information can be used for post-event analysis to guide medical treatment. Additionally, this technology can capture and provide event data that will help to provide a better understanding the mechanisms of traumatic and other brain injuries resulting from an explosion, blast, blow or other event.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method comprising:
providing a device comprising a housing having at least one sensor in an ambient environment, the at least one sensor being configured to derive a plurality of parametric signals from either a) acceleration readings generated from movement of the person, or b) pressure readings generated from perturbations propagating in the ambient environment, resulting from an identified event;
providing personal medical history data of a person that is wearing or carrying the device in the ambient environment, aggregate medical history data, and parametric data, which parametric data corresponds to the plurality of parametric signals;
tailoring and adjusting an individualized injury threshold for the person based on the personal medical history data and the aggregate medical history data;
storing the tailored and adjusted individualized injury threshold prior to the identified event;
providing in real time an injury risk assessment corresponding to the identified event by determining whether one or more of the plurality of parametric signals exceeds the stored individualized injury threshold for the person;

providing human perceivable indicia corresponding to the injury risk assessment data in response to a user assessment analysis request; and guiding medical treatment of the person when the stored individualized injury threshold is exceeded.

2. The method of claim 1, wherein the plurality of parametric signals includes at least one acceleration signal corresponding to a measured acceleration.

3. The method of claim 2, wherein the at least one acceleration signal provides three-axis acceleration data in real time.

4. The method of claim 2, wherein the at least one acceleration signal provides rotational acceleration data in real time.

5. The method of claim 1, wherein the personal medical history data corresponds to personal medical history or injuries previously sustained by the person prior to the identified event.

6. The method of claim 1, wherein the aggregate medical history data is based on group medical history data or injury assessment data obtained from other dosimetry devices over a period of time.

7. The method of claim 1, wherein the step of providing human perceivable indicia includes providing a probability that the person has sustained a predetermined injury based on the injury risk assessment data.

8. The method of claim 1, wherein the at least one sensor includes a gyroscope device.

9. The method of claim 1, wherein the at least one sensor includes a pressure sensor configured to measure air pressure based on perturbations propagating in the ambient environment.

10. The method of claim 9, wherein a control circuit is provided that is configured to compare the measured air pressure with the individualized injury threshold stored in at least one memory device to derive the injury risk assessment.

11. The method of claim 1, wherein the at least one sensor includes:
- a pressure sensor coupled to a control circuit, the pressure sensor being configured to measure air pressure based on perturbations propagating in the ambient environment;
- an inertial measurement sensor coupled to the control circuit, the inertial measurement sensor being configured to measure an acceleration of the housing in real time; and
- wherein the control circuit is configured to compare the measured air pressure and the measured acceleration with the individualized injury threshold stored in at least one memory device to derive the injury risk assessment.

12. The method of claim 1, wherein the providing in real time further comprises providing at least one memory device that includes a look-up table that obtains the injury risk assessment by relating the personal medical history data, the aggregate medical history data and the parametric data.

13. The method of claim 12, further comprising providing a control circuit configured to update the personal medical history data based on the injury risk assessment.

14. The method of claim 1, wherein the plurality of parametric signals include a date and a time stamp corresponding to an occurrence of the identified event.

15. The method of claim 1, further comprising providing a power supply configured to provide electrical energy to the device from a non-stationary or portable power source.

16. The method of claim 15, wherein the power source includes a battery device.

17. The method of claim 16, wherein the battery device is rechargeable.

18. The method of claim 15, wherein the power source includes a device configured to harvest energy from a renewable energy source.

19. The method of claim 1, wherein the at least one sensor includes a global positioning device (GPD) configured to provide GPD data corresponding to a location of the housing.

20. The method of claim 19, wherein the control circuit is configured to estimate a location of the identified event based on the GPD data and the parametric signals.

21. The method of claim 20, further comprising providing a transmitter portion configured to transmit the housing location, the identified event location, and injury risk assessment to an external receiver.

22. The method of claim 1, further comprising providing a transceiver coupled to the control circuit, the transceiver being configured to provide injury risk assessment to an external receiver.

23. The method of claim 22, wherein the transceiver is configured to receive data or instructions from an external transmitter.

24. The method of claim 1, further comprising providing a non-rechargeable or disposable battery which powers the device.

25. The method of claim 1, wherein the device is disposable after at least one I/O device has provided the injury risk assessment in response to at least one assessment analysis request.

* * * * *